(12) United States Patent
Silva (10) Patent No.: US 9,797,854 B1
(45) Date of Patent: Oct. 24, 2017

(54) RF PROBE (71) Applicant: Octavio Cesar Silva, Melbourne, FL (US)

(72) Inventor: Octavio Cesar Silva, Melbourne, FL (US)

( * ) Notice: Subject to any disclaimer, the term of this patent is extended or adjusted under 35 U.S.C. 154(b) by 155 days.

(21) Appl. No.: 14/967,363

(22) Filed: Dec. 14, 2015

(51) Int. Cl.
*G01N 27/04* (2006.01)
*G01N 27/02* (2006.01)
*G01B 7/06* (2006.01)

(52) U.S. Cl.
CPC .............. *G01N 27/041* (2013.01); *G01B 7/06* (2013.01); *G01N 27/02* (2013.01)

(58) Field of Classification Search
CPC .................................................... G01N 21/041
See application file for complete search history.

(56) References Cited

U.S. PATENT DOCUMENTS

| 5,748,002 A * | 5/1998 | Scott | G01N 22/00 324/633 |
| 2010/0315280 A1* | 12/2010 | Bakhtar | G01S 13/02 342/22 |
| 2013/0307564 A1* | 11/2013 | Colosimo | G01R 27/06 324/647 |
| 2015/0281881 A1* | 10/2015 | Appleby | E21C 39/00 715/848 |
| 2016/0061751 A1* | 3/2016 | Carr | G01N 33/383 324/637 |

* cited by examiner

*Primary Examiner* — Charlie Y Peng (57) ABSTRACT

The RF Probe is a radiofrequency device designed to determine the composition of multilayer media by transmitting pulses which are reflected at medium boundaries and received by the device. The device consists of a signal transmitter which synthesizes the probing pulses and a receiver which receives the pulses and performs processing to determine the radiometric composition of the media or objects by analyzing the phase shift of reflected pulses. The RF Probe uses a method to identify medium composition in terms of conductivity, permittivity, permeability and impedance by calculating the phase shift of reflected pulses.

10 Claims, 8 Drawing Sheets

RF PROBE

CROSS REFERENCE TO RELATED APPLICATIONS

Not applicable.

STATEMENT REGARDING FEDERALLY SPONSORED RESEARCH OR DEVELOPMENT

Not applicable.

REFERENCE TO SEQUENCE LISTING, A TABLE, OR A COMPUTER PROGRAM LISTING COMPACT DISC APPENDIX

Not Applicable.

BACKGROUND OF THE INVENTION

The present invention relates generally to radiofrequency devices and more specifically to a radiofrequency probe capable of discerning the material composition of objects.

Current technology uses spectrum absorption to determine the composition of probed objects. Objects, for example, when illuminated with X-rays reflect emissions whose spectrum is modified by their composition. The probe measures the signature of the absorption in the spectrum and is able to determine the identity of the objects. The RF Probe uses a different method by looking at the phase shift introduced a medium boundaries and computing iteratively the conductivity, permittivity, permeability and impedance.

BRIEF SUMMARY OF THE INVENTION

The RF Probe is designed to determine the composition of multilayer media. The RF Probe transmits pulses which are reflected at medium boundaries and received by the device. The device consists of a signal transmitter which synthesizes the probing pulses and a receiver which receives the pulses and performs processing to determine the radiometric composition of the media or objects by analyzing the phase shift of reflected pulses. A method to identify medium composition in terms of conductivity, permittivity, permeability and impedance by calculating the phase shift of reflected pulses is described herein.

DETAILED DESCRIPTION OF THE INVENTION

Figure 1:
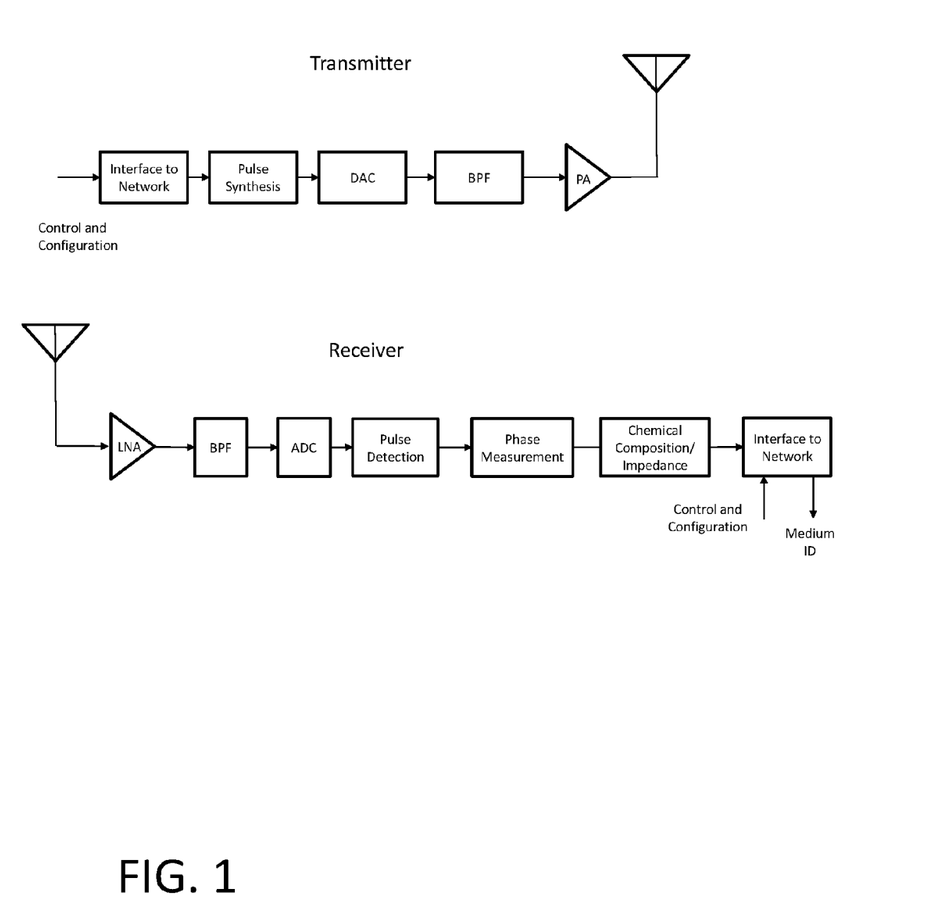
FIG. 1 shows a generalized representation of the RF Probe transmitter and receiver.

The Radar Probe architecture is shown in FIG. 1. The transmitter consists of an interface to a baseband network for control and configuration. The transmitter transmits radio frequency pulses which are digitally synthesized, converted to analog form, and amplified for transmission over the air. The transmitter is a beamforming network and can steer the transmit beam. The receiver can also steer the receive beam with a beamforming network. It receives a pulse reflected from the interface of two media. The received waveform is:

$$Y = s + v \qquad (1)$$

s is the pulse itself and v is additive white Gaussian noise. The function Y is sampled and serves as an input to the pulse detection function where the signal s is estimated and the noise v is stripped away. Then, the phase shift of the received pulse s is computed by comparing it to the transmitted pulse replica. This information is used to compute the conductivity, permeability, permittivity and impedance of the medium that caused the reflection. With that information, that medium ID or material composition is determined.

Figure 2:
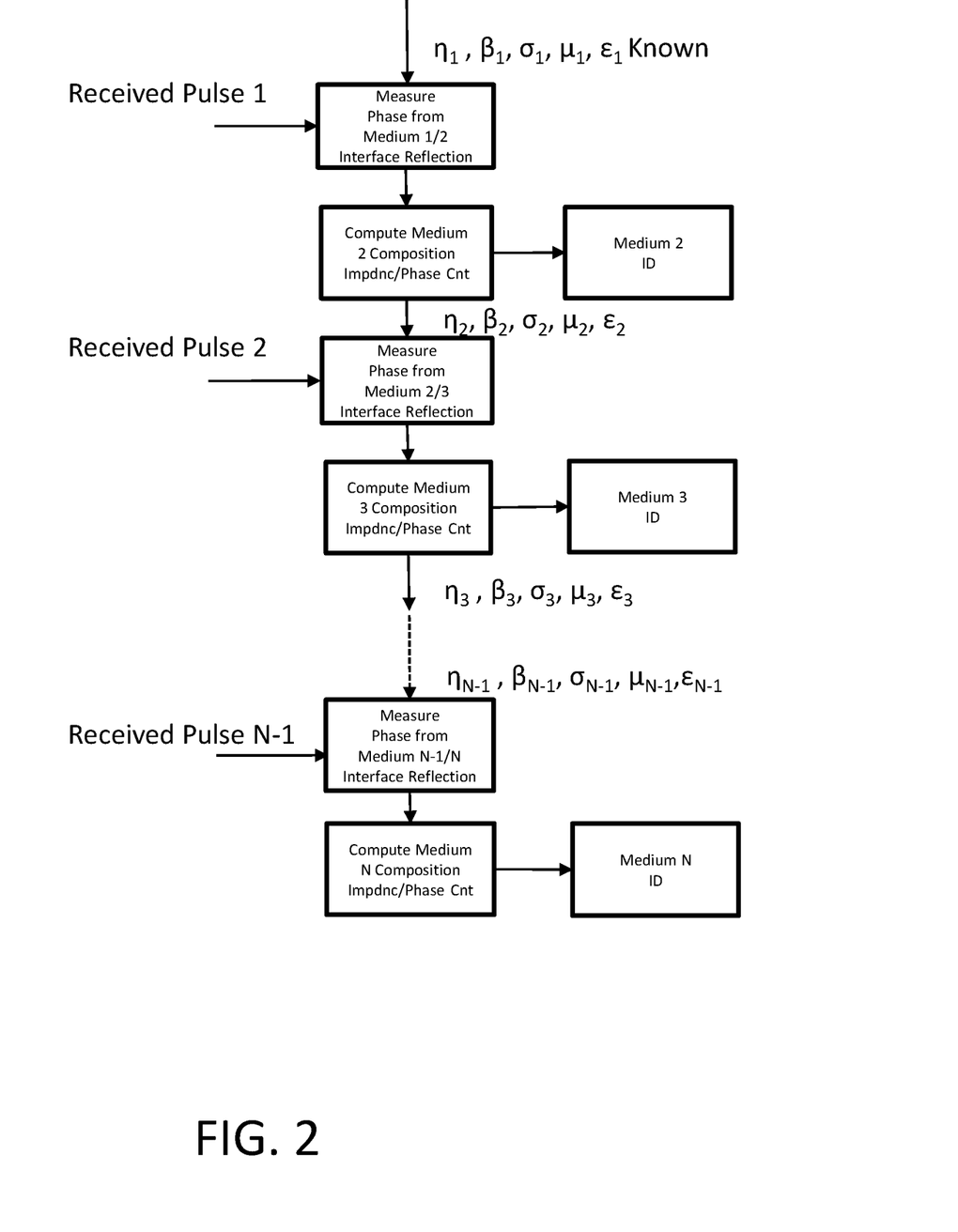
FIG. 2 shows the generalized method to determine the material composition of objects.

Pulse T1, a sine function of finite duration, is transmitted and exits the transmitter at medium 1 whose material composition (e.g. air) is known including its impedance, $\eta_1$. This is shown in FIG. 2. Medium 1 is the medium of reference. This pulse propagates in medium 1 as pulse T1 and is reflected from the interface of medium 1 and medium 2. The reflected pulse has a phase shift with respect to pulse T1. The phase shift is introduced by the reflection coefficient $\Gamma_{12}$ between medium 1 and medium 2. The phase shift of this reflected pulse (pulse R1) with respect to T1 is calculated and that information along with $\eta_1$, the conductivity, permeability and permittivity of medium 1 are used to compute the conductivity, permittivity, permeability and impedance ($\eta_2$) of medium 2.

When the transmitted pulse (pulse T1) hits the next medium boundary (medium 2-medium 3 interface), a second pulse (pulse R2) is reflected. Again, the medium 3 characteristics introduce a phase shift with respect to pulse T1 by virtue of the reflection coefficient $\Gamma_{23}$. This phase shift is calculated and that information along with the now known $\eta_2$ is used to compute the conductivity, permittivity, permeability and impedance ($\eta_3$) of medium 3. The impedance ($\eta_2$), phase constant, conductivity, permittivity, permeability of medium 2 are known from the first calculation and serve as inputs to calculate the medium 3 composition.

This process continues and, in general, the phase shift (from $\Gamma_{N\,N-1}$) of the pulse reflected at the medium N−1/medium N interface with respect to the original pulse, pulse T1, is calculated. That information along with the known impedance and characteristics of medium N−1 serve as inputs to calculate the medium N composition (conductivity, permittivity, permeability and impedance).

Figure 5:
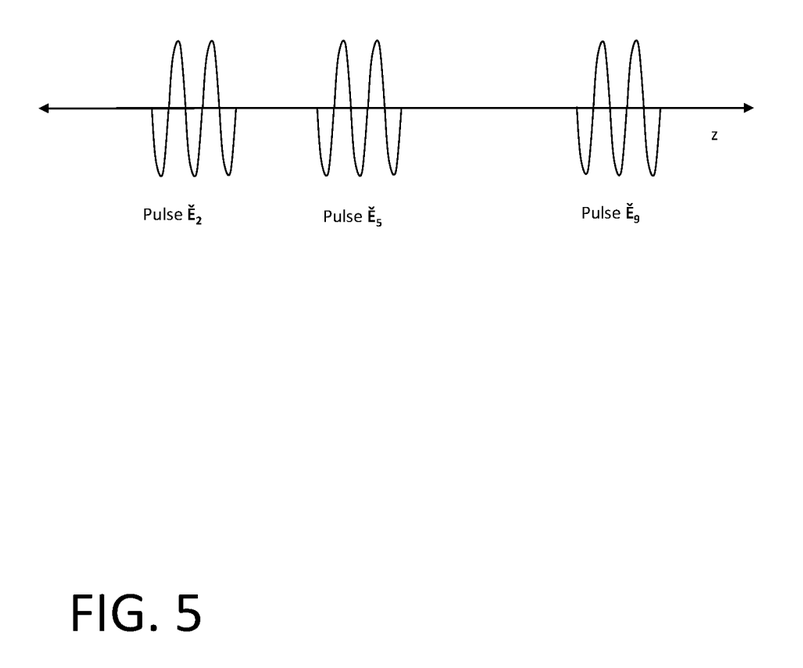
FIG. 5 shows a representation of non-overlapping pulses.
Figure 6:
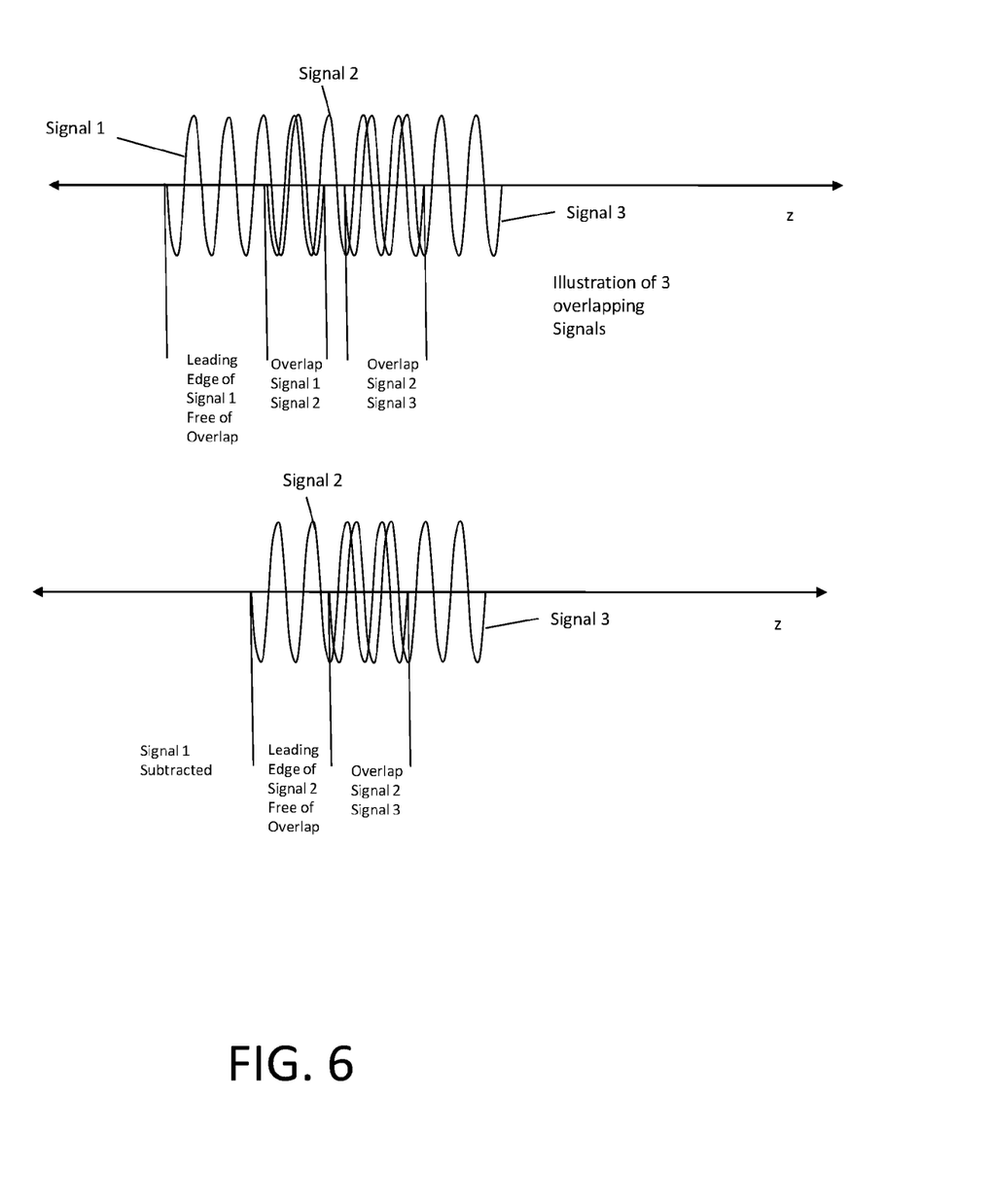
FIG. 6 shows a presentation of overlapping pulses.
Figure 7:
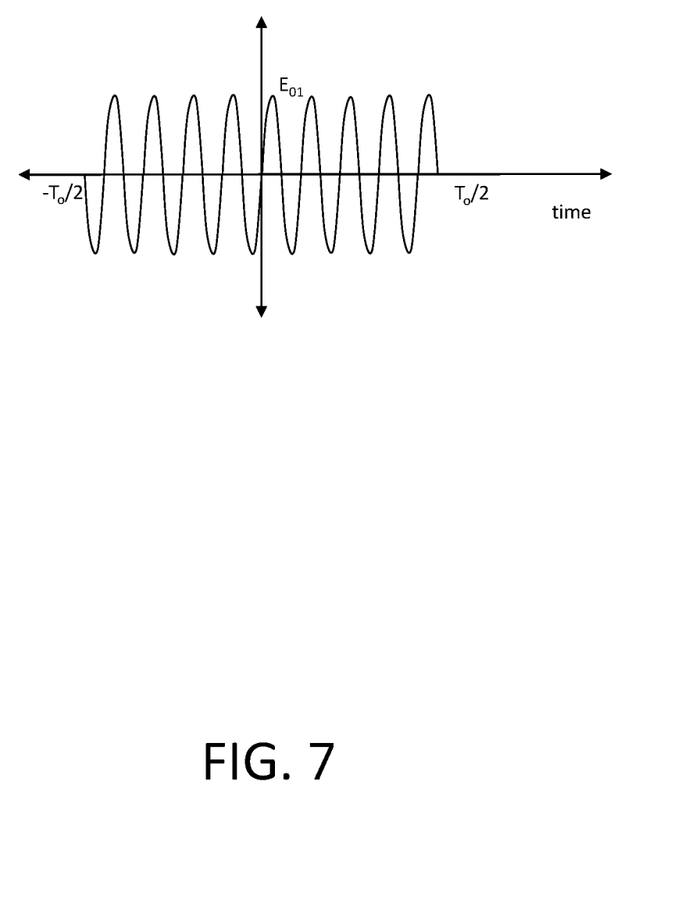
FIG. 7 shows a typical transmitted pulse.

A method to compute the composition of each medium is described herein and applies when the reflected pulses do not overlap (disjoint) and when they overlap as shown in FIG. 5 and FIG. 6.

The conductivity of a medium is determined by measuring the phase shift of the received (reflected) signal with respect to the stored replica of the original transmitted signal, $E_1(t,z)$ (vectors are shown in boldface). $E_1(t,z)$ propagates in medium 1, the medium of entry, as:

$$E_1(t,z) = \hat{x}E_{01}\sin(\omega t - \beta_1 z) = \text{Im}(\hat{x}E_{01}e^{j\omega t}e^{-j\beta_1 z}) - T_0/2 \le t \le T_0/2 \quad (2)$$

$E_{01}$ is the amplitude and is a real number
The phasor form of $E_1(t,z)$ is $$E_1(z) = \hat{x}E_{01}e^{-j\beta_1 z} \quad (3)$$

Where $\beta_1 = \omega(\mu_1\epsilon_1)^{1/2}(1+(\sigma_1/\omega\epsilon_1)^2)^{1/4}\cos\theta/2 \quad (4)$ $$\theta_1 = \tan^{-1}(\sigma_1/\omega\epsilon_1) \quad (5)$$

$T_0$ is the pulse duration
$\beta_1$ is the phase constant of medium 1 (rad/m)
z is the distance traveled
$\hat{x}$ is the unit vector in the x direction
$\omega$ is the transmission radial frequency
$\sigma_1$ is the conductivity of medium 1
$\epsilon_1$ is the permittivity of medium 1
$\mu_1$ is the permeability of medium 1.

Medium 1 is the medium of entry and reflected pulses are compared to $E_1$ to determine the phase shift with respect to it. This phase shift is used to compute the conductivity, permittivity, permeability, phase constant and impedance of a given medium.

$E_1$ exits the transmitter at medium 1 with impedance $\eta_1$ and propagates in this medium as $E_1(t,z)$. $E_1(t,z)$ is a plane wave traveling in the z+ direction in medium 1.

Figure 3:
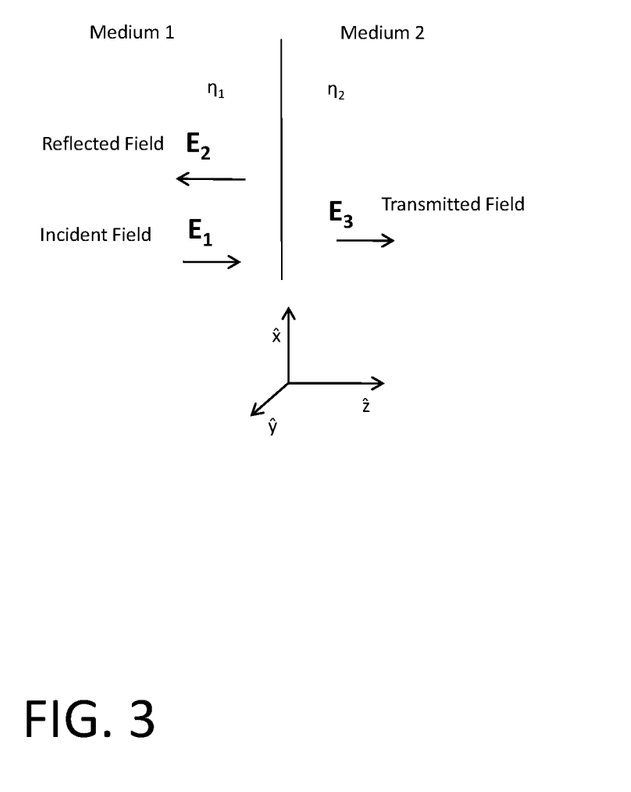
FIG. 3 shows the effects of an electric field incidence in plane medium with a different impedance resulting in a transmitted field and a reflected field.

When the $E_1$ strikes perpendicularly another plane medium with impedance $\eta_2$ two fields are created: The reflected field $E_2$ and the transmitted field $E_3$ as shown in FIG. 3 where $$E_2 = \hat{x}E_{2x} = \hat{x}E_{02}e^{j\beta_1 z} \quad (6)$$

$$E_3 = \hat{x}E_{3x} = \hat{x}E_{03}e^{-\alpha_2 z}e^{-j\beta_2 z} \quad (7)$$

$\alpha_2$ is the attenuation constant of medium 2 (Np/m)$=\omega(\mu_2\epsilon_2)^{1/2}(1+(\sigma_2/\omega\epsilon_2)^2)^{1/4}\sin\theta_2/2$ $$\theta_2 = \tan^{-1}(\sigma_2/\omega\epsilon_2) \quad (8)$$

$\beta_2$ is the phase constant in medium 2 (rad/m)
$E_{02}$ and $E_{03}$ are the amplitudes and are real numbers $$E_{02} = \Gamma_{12}E_{01} \quad (9)$$

$$E_{03} = T_{12}E_{01} \quad (10)$$

$\Gamma_{12}$ is the reflection coefficient between medium 1 and medium 2
$T_{12}$ is the transmission coefficient between medium 1 and medium 2

$$\Gamma_{12} = (\eta_2 - \eta_1)/(\eta_2 + \eta_1) \quad (11)$$

$$T_{12} = 2\eta_2/(\eta_2 + \eta_1) \quad (12)$$

$\eta_1$ is the medium 1 impedance
$\eta_2$ is the medium 2 impedance.

Without the inclusion of propagation factors which do not introduce phase shifts, $E_2$ differs from $E_1$, the original pulse, only by a factor of $\Gamma_{12}$. $\Gamma_{12}$ creates a phase shift with respect to $E_1$. The phase difference between $E_2$ and $E_1$ is measured. $E_1$ is known since it is the signal synthesized and sent by the transmitter. A replica of $E_1$ is stored in the receiver which is time synchronized with the transmitter.

In general, for medium m and medium m+1:

$$\Gamma_{m\,m+1} = (\eta_{m+1} - \eta_m)/(\eta_m + \eta_{m+1}) \quad (13)$$

$$T_{m\,m+1} = 2\eta_{m+1}/(\eta_m + \eta_{m+1}) \quad (14).$$

Consider the 4-layer example illustrated below in FIG. 4. The conductivity and thus the material make up of medium 4 (infinite for illustration purposes) is computed. Assuming that the pulses from first reflections do not overlap (FIG. 5) and that subsequent reflections within a layer are too weak and are negligible. Subsequent reflections can be neglected when the factor $e^{-\alpha z}$ is small. $\alpha$ is large when the conductivity of a given layer is large.

The propagation space loss factor and all the other gains and losses in the link are not considered because they are real and introduce no phase shift. Only the factors that produce phase shifts on the reflected signals are considered. These are the reflection coefficients, $\Gamma$, and the transmission coefficients, T. The electric field vectors used to take these factors into account are denoted in boldface with karat symbols: $\check{E}_i$.

Figure 4:
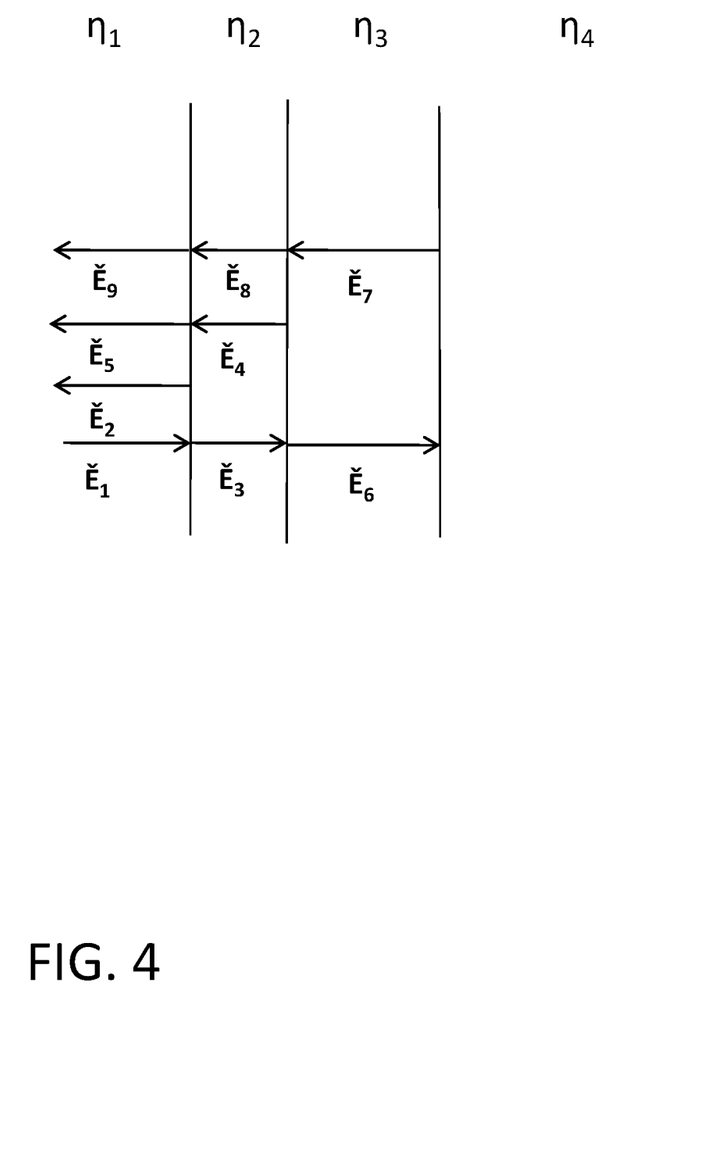
FIG. 4 shows multiple electric field reflection plane mediums of different impedances.

In FIG. 4 the following nomenclature applies:
$\check{E}_1$ the transmitted pulse which is incident at the medium 1/medium 2 boundary $$\check{E}_1 = \hat{x}E_{01}e^{-j\beta_1 z} \quad (15)$$

$\check{E}_2$ is the reflected field of $\check{E}_1$ at the medium 1/medium 2 interface
$\check{E}_3$ is the transmitted field of $\check{E}_1$ into medium 2
$\check{E}_4$ is the reflected field of $\check{E}_3$ at the medium 2/medium 3 interface
$\check{E}_5$ is the transmitted field of $\check{E}_4$ into medium 1
$\check{E}_6$ is the transmitted field of $\check{E}_3$ into medium 1
$\check{E}_7$ is the reflected field of $\check{E}_6$ at the medium 3/medium 4 interface
$\check{E}_8$ is the transmitted field of $\check{E}_7$ into medium 2
$\check{E}_9$ is the transmitted field of $\check{E}_8$ into medium 1.

Now consider $\check{E}_2$, $\check{E}_5$ and $\check{E}_9$ the first reflections at each medium boundary propagating in medium 1:

$$\check{E}_2 = \hat{x}\Gamma_{12}E_{01}e^{j\beta_1 z} = \Gamma_{12}\check{E}_1' \quad (16)$$

where $\check{E}_1' = \hat{x}E_{01}e^{j\beta_1 z} \quad (17)$ $\check{E}_1'$ is the same as $\check{E}_1$, the transmitted pulse, propagating in the opposite direction, that is, in the $-z$ direction $$\check{E}_5 = \hat{x}T_{12}T_{21}\Gamma_{23}E_{01}e^{-2\alpha_2 d_2}e^{-j2\beta_2 d_2}e^{j\beta_1 z} \quad (18)$$

$$\check{E}_9 = \hat{x}T_{12}T_{21}T_{23}T_{32}\Gamma_{34}$$
$$E_{01}e^{-2\alpha_2 d_2}e^{-j2\beta_2 d_2}e^{-2\alpha_3 d_3}e^{-j2\beta_3 d_3}e^{j\beta_1 z} \quad (19)$$

d2 is the thickness of the medium 2 layer and d3 is the thickness of the medium 3 layer.
$e^{-j2\beta_2 d_2}$ $e^{-j2\beta_3 d_3}$ are the displacement shifts with respect to $\check{E}_1'$. By calculating these displacements and the betas, d2 and d3 can be calculated.

$T_{nm}$ can be expressed as $|T_{nm}|e^{j\psi_{nm}}$ where $|T_{nm}|$ is its magnitude and $\psi_{nm}$ its phase.

$\check{E}_2$ is a replica of $\check{E}_1'$ ($\check{E}_1$) propagating in the $-z$ direction with the additional factor of $\Gamma_{12}$. $\check{E}_5$ and $\check{E}_9$ are replicas of $\check{E}_1'$ ($\check{E}_1$) propagating in the $-z$ direction with the additional factors of T, $\Gamma$, $e^{-2\alpha_i d_i}$ and $e^{-j2\beta_i d_i}$.

$\eta_1$ is known. By measuring the phase shift of the vector $\check{E}_2$ with respect to $\check{E}_1$ as explained in section 6, the conductivity ($\sigma$), permeability ($\mu$) and permittivity ($\epsilon$) of medium 2 can be determined and thus $\eta_2$.

Once $\eta_2$ and the conductivity, permeability and permittivity of medium 2 are determined, $T_{12}$ and $T_{21}$ can be calculated. $e^{-j2\beta_2 d_2}$ is the displacement shift. The magnitudes are factored out (although not necessarily) and the phases subtracted from $\check{E}_5$:

$$\check{E}_5\check{E}_5/(|T_{12}|e^{j\psi_{12}}|T_{21}|e^{j\psi_{21}}e^{-j2\beta_2 d_2}) = \hat{x}\Gamma_{23}E_{01}e^{-2\alpha_2 d_2}e^{j\beta_1 z} \quad (20)$$

$|T_{12}|$ is the magnitude of $T_{12}$ and $\psi_{12}$ its phase, and $|T_{21}|$ is the magnitude of $T_{21}$ and $\psi_{21}$ its phase.

This equation resembles the equation for $\check{E}_2=\Gamma_{12}\check{E}_1'$ in that, phase-wise, $\overline{E}_5$ and $\check{E}_1'$ (thus $\check{E}_1$) differ only by a reflection coefficient, $\Gamma_{23}$ in this case. $e^{-2\alpha 2 d2}$ is real and does not introduce a phase shift.

By measuring the phase shift of $\overline{E}_5$ with respect to the original pulse $\check{E}_1$, the conductivity and permittivity of medium 3 can be determined and thus $\eta_3$. Since we now know $T_{12}T_{21}T_{23}T_{32}$ with the calculations of $\eta_2$ and $\eta_3$, these can be taken out from $\check{E}_9$, the magnitudes factored out and the phases subtracted:

$$\overline{E}_9 = \check{E}_9/(|T_{12}|e^{j\psi 12}|T_{21}|e^{j\psi 21}|T_{23}|e^{j\psi 23}|$$
$$T_{32}|e^{j\psi 32}e^{-j2\beta 2 d2}e^{-j2\beta 3 d3}) =$$
$$\Gamma_{34}E_{01}e^{-2\alpha 2 d2}e^{-2\alpha 3 d3}\check{E}_1' \qquad (21).$$

Thus, the phase shift of $\overline{E}_9$ with respect to $\check{E}_1$ (that introduced by $\Gamma_{34}$) can be calculated to compute the conductivity, permeability, permittivity and impedance of medium 4. Therefore, the material make up of medium 4 can be determined.

In general, first reflections from a medium interface m m+1 can be put in the form:

$$\overline{E}_i = E_i/(|T_{12}|e^{j\psi 12}|T_{21}|e^{j\psi 21}|T_{23}|e^{j\psi 23}|$$
$$T_{32}|e^{j\psi 32} \ldots \ldots |T_{m-1}\ _m|e^{j\psi m-1\ m}|$$
$$T_{m\ m-1}|e^{j\psi m\ m-1}e^{-j2\beta 2 d2}e^{-j2\beta 3 d3}\ldots e^{-j2\beta m\ dm}) \qquad (22)$$

$$\overline{E}_i = \Gamma_{m\ m+1}\rho\check{E}_1' \qquad (23).$$

So, $\Gamma_{m\ m+1}$ introduces a phase shift on $\overline{E}_i$ with respect to $\check{E}_1$. $\rho$ contains the aggregate attenuation introduced by the factors $e^{-\alpha z}$ and is real, producing no phase shift. The impedances are calculated successively. Thus, all the is and all the $e^{-j2\beta m\ dm}$ can be calculated up to medium m to compute $\overline{E}_i$. Thus, with the knowledge of the phase shift introduced by $\Gamma_{m\ m+1}$ and with $\eta_m$, the conductivity, permeability, permittivity and impedance of medium m+1 can be calculated.

Now, assuming that medium 2 and medium 3 are too thin so that the reflections at the medium 2 -medium 3 and medium 3-medium 4 interfaces overlap the reflection of the medium 1-medium 2 interface. See FIG. 6. In medium 1, the electric fields add up as:

$$E_{T1} = (\rho_1 L_1 k_1 \Gamma_{12} + \rho_2 L_2 k_2 T_{12} T_{21}$$
$$\Gamma_{23} e^{-j2\beta 2 d2} + \rho_3 L_3 k_3 T_{12} T_{21} T_{23} T_{32}$$
$$\Gamma_{34} e^{-j2\beta 2 d2} e^{-j2\beta 3 d3})\check{E}_1' \qquad (24).$$

The first, second, and third terms correspond to $\check{E}_2$ (Signal 1), $\check{E}_5$ (Signal 2), $\check{E}_9$ (Signal 3) in the preceding section with the incorporation of $\rho$'s, L's and k's. The $\rho$'s are the aggregate attenuation introduced in each signal by the factor $e^{-\alpha |z|}$. Each signal experiences different attenuations as it travels through the media. For example, $\rho_3$ is the composite attenuation introduced by media 2 and 3 ($e^{-2\alpha 2 d2}\ e^{-2\alpha 3 d3}$). The $\rho$'s do not have to be necessarily computed.

The signals differ in amplitude with respect to each other. These amplitudes which include all the $\rho$'s, gains and losses in the links (the k's and the L's) are measured by the receiver. The L's are the propagation space loss factors. The other link factors, such as antenna gains, amplifier gains, filter losses are represented by the k's. Medium 1 is the medium of entry. Therefore, essentially, $\rho_1=1$. The $\rho$'s, the k's and the L's are real and do not introduce any phase shifts.

It is noted that some portion of signal 1 is unaffected by the overlap. To compute $\eta_2$, $\rho_1 L_1 k_1 \Gamma_{12}\check{E}_1'$ is reconstructed from the leading edge of the non-overlap region and the phase shift introduced by $\Gamma_{12}$ with respect to $\check{E}_1$ is calculated.

This calculation is used to compute the conductivity, permeability, permittivity and impedance of medium 2. See section 6. Now, $\rho_1 L_1 k_1 \Gamma_{12}\check{E}_1'$ is subtracted from $E_{T1}$. The new field is:

$$E_{T2} = (\rho_2 L_2 k_2 T_{12} T_{21}$$
$$\Gamma_{23} e^{-j2\beta 2 d2} + \rho_3 L_3 k_3 T_{12} T_{21} T_{23} T_{32}$$
$$\Gamma_{34} e^{-j2\beta 2 d2} e^{-j2\beta 3 d3})\check{E}_1' \qquad (25).$$

The first term is the same as $\check{E}_5$ in section 4 with the addition of $\rho_2 L_2 k_2$. With $\eta_2$ known from the first calculation, $T_{12} T_{21} e^{-j2\beta 2 d2}$ can be calculated and factored from $E_{T2}$. The resulting field is:

$$\overline{E}_{T2} = E_{T2}/(|T_{12}|e^{j\psi 12}|$$
$$T_{21}|e^{j\psi 21}e^{-j2\beta 2 d2}) = (\rho_2 L_2 k_2$$
$$\Gamma_{23} + \rho_3 L_3 k_3 T_{23} T_{32} \Gamma_{34} e^{-j2\beta 3 d3})\check{E}_1' \qquad (26).$$

The first term is the same as $\overline{E}_5$ in section 4 with the addition of $\rho_2 L_2 k_2$. $\rho_2 L_2 k_2 \Gamma_{23}\check{E}_1'$ is reconstructed from the leading edge of the non-overlap region and the phase shift introduced by $\Gamma_{23}$ with respect to $\check{E}_1$ is calculated. This calculation along with $\eta_2$ is used to compute the conductivity, permeability, permittivity and impedance of medium 3. Now, $\rho_2 L_2 k_2 \Gamma_{23}\check{E}_1'$ is subtracted from $\overline{E}_{T2}$. The resulting field is:

$$E_{T3} = \rho_3 L_3 k_3 T_{23} T_{32} \Gamma_{34} e^{-j2\beta 3 d3}\check{E}_1' \qquad (27).$$

With $\eta_3$ known, $T_{23} T_{32}$ and $e^{-j2\beta 3 d3}$ can be calculated and factored out from $E_{T3}$. The resulting field is:

$$\overline{E}_{T3} = E_{T3}/(|T_{23}|e^{j\psi 23}|T_{32}|e^{j\psi 32}e^{-j2\beta 3 d3}) = \rho_3 L_3 k_3 \Gamma_{34}\check{E}_1' \qquad (28).$$

Now, $\overline{E}_{T3}$ is free of any overlap, and $\eta_4$ can be computed by looking at the phase shift introduced by $\Gamma_{34}$ with respect to $\check{E}_1$. The conductivity, permeability, permittivity and impedance of medium 4 are calculated in the process.

Now, $\overline{E}_{T3}$ is free of any overlap, and $\eta_4$ can be computed by looking at the phase shift introduced by $\Gamma_{34}$ with respect to $\check{E}_1$. The conductivity, permeability, permittivity and impedance of medium 4 are calculated in the process.

This process can be followed for any number of overlaps as long as there are regions free of overlap in the first term of the total field and the other terms when each term is successively subtracted. Thus, for overlapping fields, the first field (term) is subtracted, then the second field (term), then the third field (term) and so on. Once each field is reconstructed from its leading edge in medium m, the conductivity, permittivity and impedance of medium m+1 is computed as described above.

The following method is used to compute the impedance, conductivity, permeability and permittivity of medium m+1. Given media m and m+1 with $\Delta$ being the phase difference between the transmitted and received pulses introduced by $\Gamma_{m\ m+1}$:

$$\tan\Delta = 2|\eta_{m+1}||\eta_m|\sin(\phi_{m+1}/2-\phi_m/2)/(|\eta_{m+1}|^2-|\eta_m|^2) \qquad (29)$$

where $$|\eta_i| = (\mu_i/\epsilon_i)^{1/2}(1+(\sigma_i/\omega\epsilon_i)^2)^{-1/4} \qquad (30)$$

$$\phi_i = \tan^{-1}(\sigma_i/\omega\epsilon_i) \qquad (31)$$

This equation is solved for $\mu_i$ and $\sigma_i/\epsilon_i$.

Once the composition of medium m+1 is identified, $\eta_{m+1}$ is found by the following formula:

$$\eta_{m+1} = (\mu_{m+1}/\epsilon_{m+1})^{1/2}(1+(\sigma_{m+1}/\omega\epsilon_{m+1})^2)^{-1/4}(\cos(\phi_{m+1}/2)+j\sin(\phi_{m+1}/2)) \qquad (32)$$

$$\phi_{m+1}\tan^{-1}(\sigma_{m+1}/\omega\epsilon_{m+1}) \qquad (33)$$

Time-wise, a layer with thickness d will produce a subsequent reflection (from the interface with the next layer below) that lags the first reflection by $t_1=2\ d/v=2\ d/(\omega/\beta)$, where v is the velocity of the pulse in the medium and $\beta$ is the phase constant of the medium. The next subsequent reflection lags the first reflection by $t_2=4\ d/v$ and so on. In general, the time position of these reflections with respect to $t_1$ are $t_1$ (first), $2t_1$ (second), $4t_1$ (third), $6t_1$ (fourth) and so on.

In many cases, the layer is lossy and only the first or second subsequent reflections are taken into account since further subsequent reflections are too attenuated by the medium and are negligible.

Figure 8:
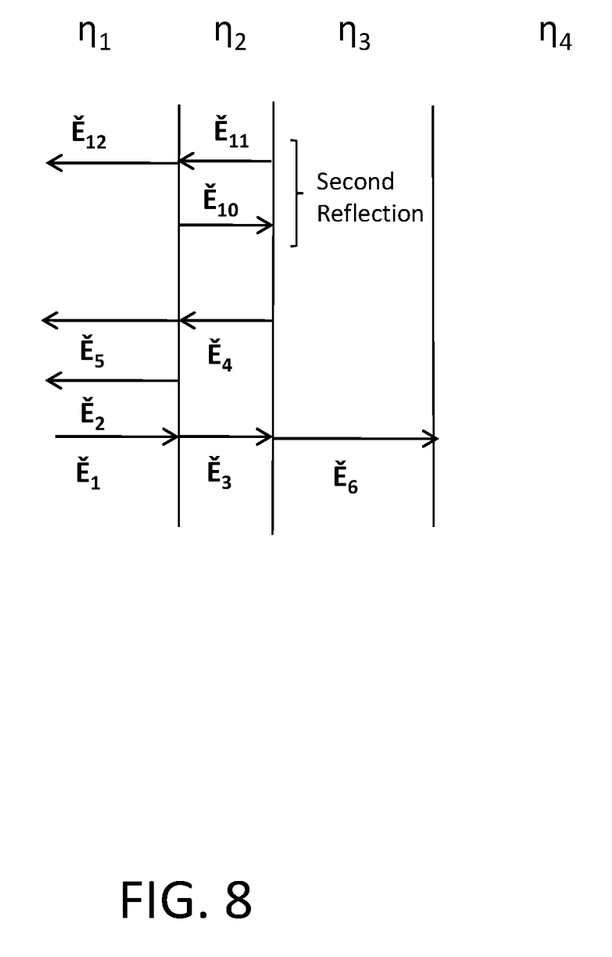
FIG. 8 shows the morphology of second reflections in a given plane medium.

Consider FIG. 8 for the case of non-overlapping pulses, taking into account only the terms that cause phase shifts. This is the same as FIG. 4 with the first two first-reflections $\check{E}_2$ and $\check{E}_5$, which are the fields described in section 4:

$\check{E}_{12}$, propagating in medium 1, is the second reflection (first subsequent reflection) of $\check{E}_5$ from the medium 2/medium 3 interface.

$\check{E}_{10}$ is the reflected field of $\check{E}_4$ at the medium 2/medium 1 interface $\check{E}_{11}$ is the reflected field of $\check{E}_{10}$ at the medium 2/medium 3 interface $\check{E}_{12}$ is the transmitted field of $\check{E}_{11}$ into medium 1

$$\check{E}_{12}=\Gamma_{21}\Gamma_{23}e^{-2\alpha 2 d2}e^{-j2\beta 2 d2}\check{E}_5 \qquad (34).$$

$\check{E}_{12}$ is subtracted by determining its position in the reflection chain. With respect to $\check{E}_5$, this position is given timewise by $t_1=2\ d_2/(\omega/\beta_2)$ (35).

$\check{E}_5$ is the first reflection from the medium 2/medium 3 interface. If there is an overlap with other fields, $\check{E}_{12}$ can be subtracted by calculating $\Gamma_{21}\Gamma_{23}e^{-2\alpha 2 d1}e^{-j2\beta 2 d1}$ the method of section 5. In general, subsequent reflections of first reflection $\check{E}_x$ in a given layer m are of the form:

$$\check{E}_i = \Gamma_{m\ m-1}^{p/2} e^{-p\ \alpha m\ dm} e^{-jp\ \beta m\ dm} \check{E}_x \qquad (35)$$

Where $\alpha_m$ is the attenuation constant, $\beta_m$ is the phase const., $d_m$ is the thickness of medium m and p is an even number. p=2 (first subsequent reflection), p=4 (second subsequent reflection) and so on.

The thickness of medium 2 in section 4 can be calculated by measuring the time delay, $t_1$, between $\check{E}_2$ and $\check{E}_5$ $$\check{E}_2 = \hat{x}T_{12}E_{01}e^{j\beta 1 z} = \Gamma_{12}\check{E}_1' \qquad (36)$$

$$\check{E}_5 = \hat{x}T_{12}T_{21}\Gamma_{23}E_{01}e^{-2\alpha 2 d2}e^{-j2\beta 2 d2}e^{j\beta 1 z} \qquad (37)$$

$$d2=\omega t_1/2\beta_2 \qquad (38).$$

In general the time delay for a given pulse with respect to $\check{E}_2$ is:

$$t_n = t_1+t_2+t_3+ \ldots t_{n-1}+2\beta_{n+1}d_{n+1}/\omega \qquad (39)$$

$$\text{where } t_i=2\beta_{i+1}d_{i+1}/\omega \qquad (40).$$

The n+1 pulse contains all the displacements delays of the previous pulses. Each previous $t_i$ is subtracted from the total time delay ($t_n$) of the n+1 pulse. Thus:

$$t_n'=t_n-(t_1+t_2+t_3+ \ldots t_{n-1})=2\beta_{n+1}d_{n+1}/\omega \qquad (41)$$

$$d_{n+1}=\omega t_n'/2\beta_{n+1} \qquad (42)$$

The invention claimed is:

1. A radiofrequency detection device for detecting the material composition of multilayer media by outwardly transmitting a radiofrequency pulse and detecting the electrical properties of said multilayer media based on the reflections of such radiofrequency pulse from the layered composition of said multilayer media, comprising: a transmitter composed of a pulse synthesis module that creates a predetermined digital sinusoid function representation of said radiofrequency pulse, a digital to analog conversion device that converts the sampled representation of said radiofrequency pulse to analog form, a first band-pass filter, a power amplifier to transmit said radiofrequency pulse at a predetermined power level, an antenna with predetermined radiation characteristics to outwardly radiate said radiofrequency pulse, and a network interface module that interfaces to a computing device to control and configure said transmitter to predetermined transmit parameters; a receiver composed of a receiving antenna with predetermined receiving characteristics to receive the multiple reflections of said radiofrequency pulse, a low noise amplifier to amplify said multiple reflections of said radiofrequency pulse at a predetermined level, a second bandpass filter, an analog to digital conversion device to sample said multiple reflections of said radiofrequency pulse, a pulse detection module that reconstructs said multiple reflections, a phase and delay measurement module that iteratively computes the phase of the said multiple reflections of said radiofrequency pulse in a non-overlapping and overlapping manner and the thickness of a given layer based on measured delays as a result of reflections from the layers boundaries of said multilayer media, a material composition detection module that identifies the material composition of the layers that compose said multilayer media by calculating their conductivity, permeability and permittivity based on the phase measurements of said multiple reflections, and the network interface module that interfaces to a computing device to transmit in the form of data the identification of the layers of said multilayer media.

2. A method to identify the material composition of multilayer media by calculating their conductivity, permeability and permittivity, and the thickness of the composing layers of said multilayer media by transmitting a radiofrequency pulse and receiving the reflections of such radiofrequency pulse in an non-overlapping and overlapping manner, comprising the steps of: Measuring the phase shift from the incidence of said radiofrequency pulse at the interface between medium 1 and medium 2 thereby computing the conductivity, permeability, permittivity, impedance and phase constant of medium 2 given the conductivity, permeability, permittivity, impedance and phase constant of medium 1 and thus identifying the material composition of medium 2 and the thickness of medium 1 from the transit delay of said radiofrequency pulse in medium 1; measuring the phase shift from the incidence at the interface between medium 2 and medium 3 thereby computing the conductivity, permeability, permittivity, impedance and phase constant of medium 3 and thickness of medium 2 given the conductivity, permeability, permittivity, impedance and phase constant of medium 2 and thus identifying the material composition of medium 3 and the thickness of medium 2 from the transit delay of said radiofrequency pulse in medium 2; measuring the phase shift from the incidence at the interface between medium 3 and medium 4 thereby computing the conductivity, permeability, permittivity, impedance and phase constant of medium 4 and the thickness of medium 3 given the conductivity, permeability, permittivity, impedance and phase constant of medium 3 and thus identifying the material composition of medium 4 and the thickness of medium 3 from the transit delay of said radiofrequency pulse in medium 4; and iteratively measuring the phase shift from the incidence at the interface between medium n and medium n+1 thereby computing the conductivity, permeability, permittivity, impedance and phase constant of medium n+1 and the thickness of medium n given the conductivity, permeability, permittivity, impedance and phase constant of medium n and thus identifying the material composition of medium n+1 and the thickness of medium n from the transit delay of said radiofrequency pulse in medium n.

3. The method in claim 2 wherein the phase shift A between the transmitted radiofrequency pulse and the received radiofrequency pulses introduced by the reflection coefficient $\Gamma_{m\ m+1}$ between layer m and m+1 is computed to solve for the conductivity, permeability, permittivity of medium m+1 to satisfy the following condition (1)

$$\tan\Delta = 2|\eta_{m+1}||\eta_m|\sin(\phi_{m+1}/2 - \phi_m/2)/(|\eta_{m+1}|^2 - |\eta_m|^2) \quad (1);$$

wherein $$\eta_m = (\mu_m/\epsilon_m)^{1/2}(1+(\sigma_m/\omega\epsilon_m)^2)^{-1/4}(\cos(\phi_m/2)+j\sin(\phi_m/2)) \quad (2);$$

wherein $$\phi_m = \tan^{-1}(\sigma_m/\omega\epsilon_m) \quad (3);$$

wherein $$\eta_{m+1} = (\mu_{m+1}/\epsilon_{m+1})^{1/2}(1+(\sigma_{m+1}/\omega\epsilon_{m+1})^2)^{-1/4}(\cos(\phi_{m+1}/2)+j\sin(\phi_{m+1}/2)) \quad (4);$$

wherein $$\phi_{m+1} = \tan^{-1}(\sigma_{m+1}/\omega\epsilon_{m+1}) \quad (5);$$

wherein $\eta_m$ is the complex impedance of medium m with absolute value $|\eta_m|$ and $\phi_m$ is the phase of said complex impedance $\eta_m$;
wherein $\eta_{m+1}$ is the complex impedance of medium m+1 with absolute value $|\eta_{m+1}|$ and $\phi_{m+1}$ is the phase of said complex impedance $\eta_{m+1}$;
wherein $\mu_m$, $\epsilon_m$, and $\sigma_m$ are the permeability, permittivity, conductivity, respectively, of medium m;
wherein $\mu_{m+1}$, $\epsilon_{m+1}$ and $\sigma_{m+1}$ are the permeability, permittivity, conductivity, respectively, of medium m+1;
wherein $\omega$ is the pulse angular frequency.

4. The method in claim 2 where the conductivity, permeability, permittivity of medium m+1 is computed for non-overlapping pulses by looking at first reflections from said medium m+1 wherein said first reflections satisfy condition (6)

$$\bar{E}_i = \Gamma_{m\ m+1}\rho\check{E}_1' \quad (6);$$

wherein $\bar{E}_i$ is the reflected pulse between layer m and m+1;
wherein $\check{E}_1'$ is the first transmitted pulse traveling in the opposite direction;
wherein $\Gamma_{m\ m+1}$ is the reflection coefficient between medium m and m+1;
and wherein $\rho$ contains the aggregate attenuation of all the intervening layers for E.

5. The method of claim 2 where the conductivity, permeability, permittivity and impedance of medium 2 is computed for overlapping pulses by looking at the leading edge of the non-overlapping section of the first received pulse, extracting the reflection coefficient between medium 1 and 2 and subtracting the first pulse from the total received signal.

6. The method of claim 5 where the conductivity, permeability, permittivity and impedance of medium 3 is computed for overlapping pulses by looking at the leading edge of the non-overlapping section of the second received pulse which satisfies condition (7)

$$E_{T2} = (\rho_2 L_2 k_2 \Gamma_{23} + \rho_3 L_3 k_3 T_{23} T_{32} \Gamma_{34} e^{-j2\beta_3 d_3})\check{E}_1' \quad (7);$$

measuring the phase shift of the reflection coefficient $\Gamma_{23}$ between medium 2 and medium 3 to compute the conductivity, permeability, permittivity and impedance of medium 3 with the knowledge of the impedance of medium 2 and subtracting the second received pulse from the total received signal;
wherein $E_{T2}$ is the factored out total field composed of the second received pulse and the third received pulse;
wherein $\check{E}_1'$ is the first transmitted pulse traveling in the opposite direction;
wherein $\Gamma_{3\ 4}$ is the reflection coefficient between medium 3 and 4;
wherein $T_{23}$ is the transmission coefficient between medium 2 and 3;
wherein $T_{32}$ is the transmission coefficient between medium 3 and 2;
wherein $\beta 3$ is the phase constant of medium 3;
wherein d3 the thickness of layer 3;
wherein L2 is the propagation space loss factor for the second received pulse;
wherein L3 is the propagation space loss factor for the third received pulse;
wherein k2 represents the intervening device gains or losses, including antenna gains, amplifier gains and filter losses for the second received pulse;
wherein k3 represents the intervening device gains or losses, including antenna gains, amplifier gains and filter losses for the third received pulse;
wherein $\rho 2$ contains the aggregate attenuation of all the intervening layers for the second received pulse;
and wherein $\rho 3$ contains the aggregate attenuation of all the intervening layers for the third reflected pulse.

7. The method of claim 6 where the conductivity, permeability, permittivity and impedance of medium m+1 is computed for overlapping pulses by looking at the leading edge of the non-overlapping section of the mth received pulse to satisfy contidion (8)

$$E_{Tm} = (\rho_m L_m k_m \Gamma_{m\ m+1} + \rho_{m+1} L_{m+1} k_{m+1} T_{m\ m+1} T_{m+1\ m} \Gamma_{m+1\ m+2} e^{-j2\beta_{m+1} d_{m+1}})\check{E}_1' \quad (8);$$

measuring the phase of the reflection coefficient $\Gamma_{m\ m+1}$ to compute the conductivity, permeability, permittivity and impedance of medium m+1 with the knowledge of the impedance of medium m and subtracting pulse mth from the total received signal;
wherein $E_{Tm}$ is sum of the mth received pulse and the (m+1)th received pulse;
wherein $\check{E}_1'$ is the first transmitted pulse traveling in the opposite direction;
wherein $\Gamma_{m+1\ m+2}$ is the reflection coefficient between medium m+1 and m+2;
wherein $T_{m\ +m+1}$ is the transmission coefficient between medium m and m+1;
wherein $T_{m+1\ m}$ is the transmission coefficient between medium m+1 and m;
wherein $\beta m+1$ is the phase constant of medium m+1;
wherein dm+1 the thickness of layer m+1;
wherein The Lm is the propagation space loss factor for the mth received pulse;
wherein Lm+1 is the propagation space loss factor for the (m+1)th received pulse;
wherein km are intervening devices gain or loss, including antenna gains, amplifier gains and filter losses for the mth received pulse;
wherein k(m+1)i are intervening devices gain or loss, including antenna gains, amplifier gains and filter losses for the (m+1)th received pulse;
wherein $\rho m$ contains the aggregate attenuation of all the intervening layers for the mth received pulse;

and wherein ρm+1 contains the aggregate attenuation of all the intervening layers for the (m+1)th received pulse.

8. The method of method of claim 7 where the conductivity, permeability, permittivity and impedance of the last infinite medium v is computed for overlapping pulses by looking at the leading edge of the non-overlapping section of the contiguous sth received pulse to satisfy condition (9)

$$E_{TN} = \rho_s L_s k_s \Gamma_{s,v} \check{E}_1' \qquad (9);$$

measuring the phase of the reflection coefficient $\Gamma_{s,v}$ to compute the conductivity, permeability, permittivity and impedance of medium v with the knowledge of the impedance of medium s;

wherein $E_{TN}$ is the received signal from the incidence between medium s an v;

wherein $\check{E}_1'$ is the first transmitted pulse traveling in the opposite direction;

wherein $F_{s,v}$ is the reflection coefficient between medium s and v;

wherein The Ls is the propagation space loss factor for the pulse reflected between medium s and medium v;

wherein ks are intervening devices gain or loss, including antenna gains, amplifier gains and filter losses for the pulse reflected between medium s and v;

and wherein ρs contains the aggregate attenuation of all the intervening layers for the pulse reflected between medium s and medium v.

9. The method in claim 2 where subsequent reflections of the first reflection $\check{E}_x$ in a given layer m satisfy condition (10)

$$\check{E}_i = \Gamma_{m\ m-1}^{p/2} \Gamma_{m\ m+1}^{p/2} e^{-p\ \alpha m\ dm} e^{-jp\ \beta m\ dm} \check{E}_x \qquad (10);$$

wherein said subsequent reflections satisfy condition (11)

$$\Gamma_{m\ m-1}^{p/2} \Gamma_{m\ m+1}^{p/2} e^{-p\ \alpha m\ dm} e^{-jp\ \beta m\ dm} \qquad (11);$$

wherein $\check{E}_i$ is the subsequent reflection between layers m and m+1;

wherein $\alpha_m$ is the attenuation constant, $\beta_m$ is the phase constant, $d_m$ is the thickness of medium m, and p is an even number, wherein p=2 for first subsequent reflection and wherein p=4 for second subsequent reflection.

10. The method of claim 2 where the thickness $d_{n+1}$ of medium n+1 satisfies condition (12)

$$d_{n+1} = \omega t_n'/2\beta_{n+1} \qquad (12);$$

$$\text{wherein } t_n' = t_n - (t_1 + t_2 + t_3 + \ldots t_{n-1}) = 2\beta_{n+1} d_{n+1}/\omega \qquad (13);$$

$$\text{wherein } t_n = t_1 + t_2 + t_3 + \ldots t_{n-1} + 2\beta_{n+1} d_{n+1}/\omega \qquad (14);$$

$$\text{wherein } t_1 = 2\beta_{i+1} d_{i+1}/\omega \qquad (15);$$

wherein ω is the pulse angular frequency;
wherein $t_i$ is the time delay of medium ith;
Wherein $\beta_{i+1}$ is the phase constant of medium i+1;
Wherein $d_{i+1}$ is the thickness of medium i+1.

* * * * *